United States Patent
Gustafsson et al.

(10) Patent No.: US 9,468,507 B2
(45) Date of Patent: Oct. 18, 2016

(54) INSERTION TOOL

(71) Applicant: STRAUMANN HOLDING AG, Basel (CH)

(72) Inventors: Emilia Gustafsson, Zurich (CH); Florian Dalla Torre, Liestal (CH); Miodrag Lazic, Oberdorf (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 14/433,249

(22) PCT Filed: Sep. 19, 2013

(86) PCT No.: PCT/EP2013/002823
§ 371 (c)(1),
(2) Date: Apr. 2, 2015

(87) PCT Pub. No.: WO2014/053218
PCT Pub. Date: Apr. 10, 2014

(65) Prior Publication Data
US 2015/0250565 A1 Sep. 10, 2015

(30) Foreign Application Priority Data
Oct. 2, 2012 (EP) .................................. 12006866

(51) Int. Cl.
A61C 1/14 (2006.01)
A61C 8/00 (2006.01)
B25B 23/14 (2006.01)

(52) U.S. Cl.
CPC ............... A61C 8/0089 (2013.01); A61C 1/14 (2013.01); B25B 23/1415 (2013.01)

(58) Field of Classification Search
CPC .... A61C 8/0089; A61C 8/0087; A61C 1/14; B25B 23/1415

USPC .......................... 433/127, 141, 163, 173, 174
See application file for complete search history.

(56) References Cited

U.S. PATENT DOCUMENTS 5,295,831 A * 3/1994 Patterson ............. A61C 8/0089
  433/141
5,328,371 A * 7/1994 Hund ..................... A61C 8/005
  433/173

(Continued)

FOREIGN PATENT DOCUMENTS

EP 1004284 A2 5/2000
WO 2012/066524 A1 5/2012

OTHER PUBLICATIONS

Mar. 20, 2014 International Search Report issued in International Patent Application No. PCT/EP2013/002823.
Apr. 7, 2015 International Preliminary Report on Patentability issued in Application No. PCT/EP2013/002823.

*Primary Examiner* — Nicholas Lucchesi
(74) *Attorney, Agent, or Firm* — Oliff PLC

(57) ABSTRACT

Insertion tool for transmitting torque from a drive tool to a dental implant, having a tool shaft including, at its apical end a dental implant engagement section including a torque applying unit to engage the dental implant such that torque can be transmitted from the insertion tool to the implant, a drive tool engagement section coronal of the dental implant engagement section including a primary torque receiving unit to engage the drive tool such that torque can be transmitted from the drive tool to the insertion tool, and a break zone arranged between the drive tool and dental implant engagement sections and designed to break upon application of a predetermined amount of torque. The shaft includes, between the dental implant engagement section and the break zone, an auxiliary torque receiving unit to engage a drive tool such that torque can be transmitted from the drive tool to the insertion tool.

14 Claims, 9 Drawing Sheets

(56) References Cited

U.S. PATENT DOCUMENTS

| | | | | |
|---|---|---|---|---|
| 5,366,412 A | * | 11/1994 | Beaty | F16D 7/08 433/173 |
| 5,782,918 A | * | 7/1998 | Klardie | A61C 8/005 433/172 |
| 5,951,287 A | * | 9/1999 | Hawkinson | A61C 8/005 433/141 |
| 6,308,598 B1 | | 10/2001 | O'Neil | |
| 6,312,260 B1 | * | 11/2001 | Kumar | A61C 8/008 206/368 |
| 6,454,567 B1 | * | 9/2002 | Carchidi | A61C 8/0089 433/141 |
| 8,070,491 B2 | * | 12/2011 | Mundwiler | A61C 8/0087 206/63.5 |
| 8,827,702 B2 | * | 9/2014 | Mamraev | A61C 8/0087 206/368 |
| 9,119,688 B2 | * | 9/2015 | Kenk | A61C 8/0087 |
| 9,179,989 B2 | * | 11/2015 | Mullaly | A61C 13/2656 |
| 2006/0269890 A1 | | 11/2006 | Mundwiler et al. | |
| 2007/0190490 A1 | * | 8/2007 | Giorno | A61C 8/0022 433/173 |
| 2007/0287129 A1 | * | 12/2007 | Ihde | A61C 8/001 433/174 |
| 2008/0102420 A1 | | 5/2008 | Porter et al. | |
| 2011/0143315 A1 | | 6/2011 | Guenter et al. | |
| 2011/0223557 A1 | * | 9/2011 | Anitua Aldecoa | A61C 8/0089 433/141 |
| 2011/0277601 A1 | | 11/2011 | Daglow | |
| 2012/0171638 A1 | * | 7/2012 | Guenter | A61C 8/0087 433/163 |
| 2012/0196247 A1 | * | 8/2012 | Bugnard | A61C 8/0066 433/141 |
| 2013/0065197 A1 | * | 3/2013 | Mamraev | A61C 8/0087 433/147 |
| 2013/0230825 A1 | * | 9/2013 | Kenk | A61C 8/0089 433/163 |

\* cited by examiner

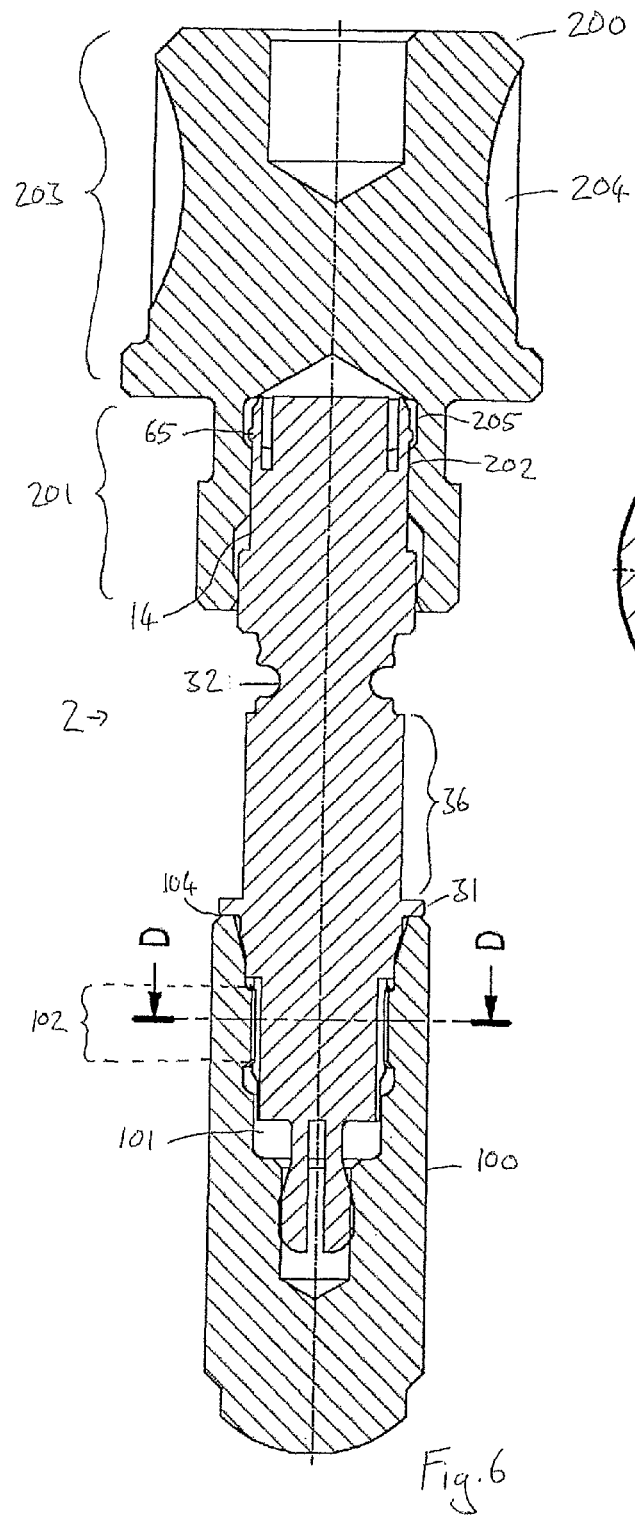
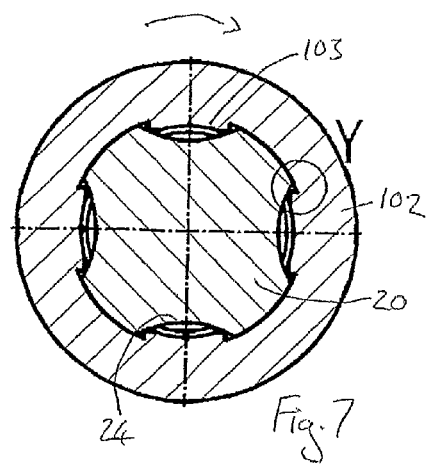
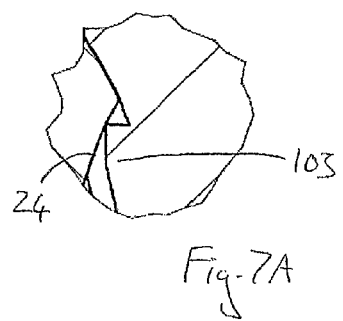

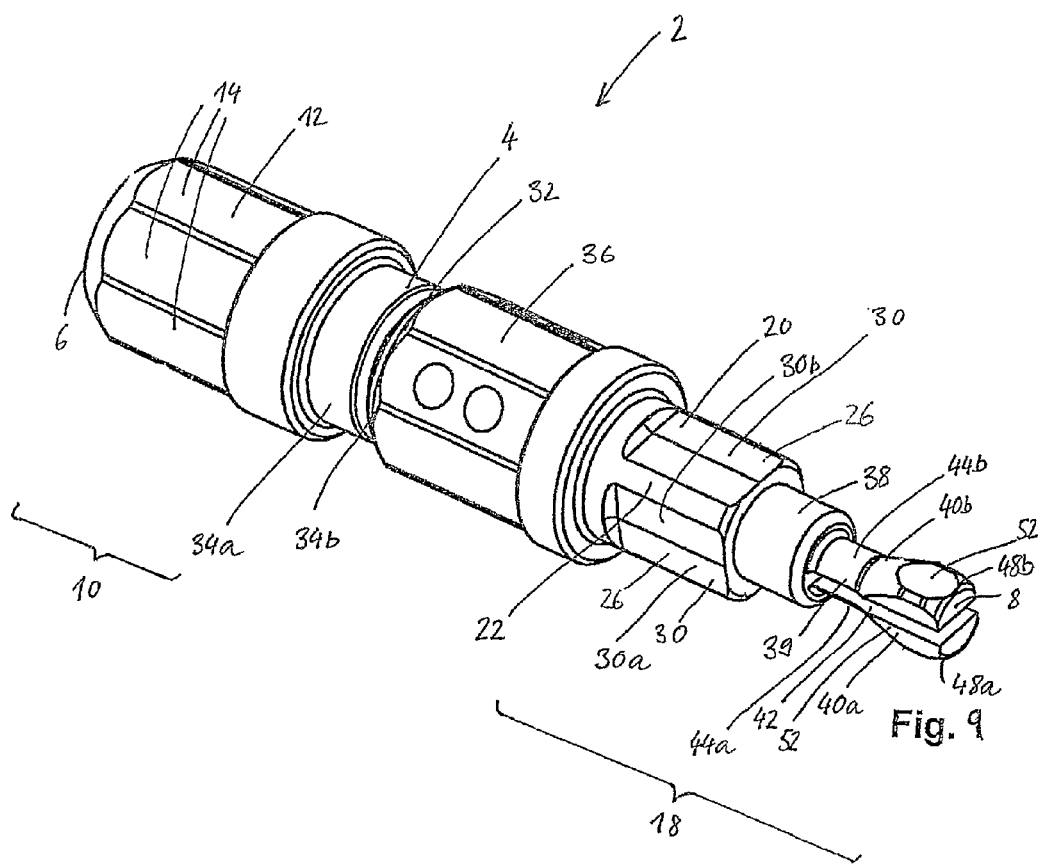

INSERTION TOOL

The present invention relates to an insertion tool according to the preamble of claim 1.

In oral implantology, dental implants are used to replace individual teeth or for anchoring more complex structures, which generally replace several or even all of the teeth. The majority of commercially available implants comprise a threaded shank which is screwed into a prepared implantation site in the bone. The threads provide the implant with primary stability until the implant is incorporated (osseointegrated) into the bone structure.

Insertion tools are used for screwing the implant into the bone by means of a drive tool, such as a ratchet, wrench or motorised dental handpiece. Insertion tools are often also used to transport a dental implant from its packaging to the implant site and, when the insertion tool is packaged with the implant, it also acts to hold the implant in place within the package. This form of insertion tool is sometimes referred to as a "transfer piece".

To fulfill its purpose, the insertion tool must be capable of transferring torque from the drive tool to the implant as well as, in some cases, remaining axially connected to the implant during storage and/or transport.

Insertion tools therefore comprise a torque applying means shaped to engage the implant in a torque transmitting manner. Torque can for example be transmitted via a friction fit between the tool and the implant, e.g. using complementary conical tapers.

However, in many implant systems the main bulk of torque transfer occurs via a geometrical fit between the two components.

In such systems, the implant comprises either an internal or external anti-rotation means. An external anti-rotation means is usually formed at the coronal most end of the implant, whereas an internal anti-rotation means is usually located within an axial bore which extends apically into the implant from its coronal end. The anti-rotation means has a non-circular cross-section in a plane perpendicular to the longitudinal axis of the implant. This means that the anti-rotation means has some cross-sectional surface areas which are not circular about the longitudinal axis i.e., it does not have a uniform radial length. For example, the anti-rotation means may have a cross-section in the form of a polygon, which provides a number of planar sides angularly spaced about the longitudinal axis of the implant. Alternatively the anti-rotation means may comprise a number of radially extending grooves or protrusions, which can be curved or planar. These non-circular surfaces of the anti-rotation means are referred to herein as "anti-rotation surfaces".

The co-operating insertion tools of such systems comprise a torque applying means having a non-circular cross-section in a plane perpendicular to the longitudinal axis of the insertion tool, at least one non-circular surface of which complements an anti-rotation surface of the implant anti-rotation means. When the tool is inserted into or over the anti-rotation means of the implant therefore, these surfaces align in a non-relative-rotational manner which enables torque to be transmitted to the implant. The surface(s) of the torque applying means which cooperate with the anti-rotation surface(s) of the implant are herein referred to as "torque applying surface(s)".

By "complements" or "complementary" it is not required that the torque applying means and anti-rotation means have matching cross-sections, or even matching torque applying and anti-rotation surfaces, only that these can engage one another in a rotationally locked manner such that rotation of the insertion tool results in rotation of the implant.

The insertion tool acts to indirectly connect the implant to a standard drive tool, such as a dental handpiece, ratchet etc. The insertion tool can thus also be viewed as an adapter, enabling standard drive tools to be used to apply torque to a specific implant design.

At their proximal end therefore insertion tools generally comprise a torque receiving means which is shaped to engage and cooperate in a torque transmitting manner with the drive tool. In a similar manner to the torque applying means, the torque receiving means comprises a non-circular cross-section, resulting in the creation of at least one torque receiving surface. The shape of the cross-section is designed to complement the driving means of the drive tool. This driving means is usually located at the distal most end of the drive tool and has the form of either a hollow sleeve with an internal wall having a non-circular cross-section or a bolt having an external non-circular cross-section, resulting in the creation of at least one torque transmitting surface. The torque receiving means is complementary such that it can be inserted into or over the driving means of the drive tool such that the non-circular cross-sections align in a rotationally locked manner. This means that when the distal end of the drive tool is rotated the insertion tool is similarly rotated, allowing torque to be transmitted to the implant.

During insertion of the implant into the bone, it is possible that the surgeon will apply too much torque, which can lead to damage of the implant and—more severely—of the bone. Such damage includes distortion of the implant anti-rotation means, which can lead to jamming of the insertion tool and can also prevent or loosen the connection between the implant and secondary components, such as abutments or prostheses, which also utilise the anti-rotation means to form a rotationally fixed connection to the implant. In severe cases the implant can break, causing damage to the surrounding bone tissue and making it difficult to remove the implant from the bone. In order to avoid this, it is important that the insertion tool breaks before damage to the implant or bone occurs.

For this reason, insertion tools comprising a break zone are known. The break zone is a zone of weakness on the tool shaft, such as a section of reduced diameter, which will break upon application of a pre-determined amount of torque and thus prevent any further transmittal of torque to the implant.

A tool for transmitting torque to a dental implant having a zone of weakness, in which the tool deforms above a predetermined breaking point, is e.g. disclosed in US-A-2011/0143315.

Further, EP-A-1004284 discloses a modular torque-applying surgical tool comprising a driver member and a torque-applying insert attachable to the driver member, the insert being deformable when subjected to a torque at or above a predetermined magnitude.

An insertion tool according to the concept of e.g. EP-A-1004284 has the disadvantage that it needs to be replaced when deformation or breakage occurs. Only after replacement can the surgeon continue to manipulate the dental implant, i.e. removing it from the implantation site or inserting it further, although this latter practice is generally not advised.

Replacement includes a first step of releasing the deformed or broken insertion tool from the dental implant and a second step of engaging an additional (intact) insertion tool with the dental implant. Both steps can be relatively complex, given the fact that they have to be performed during surgery.

Moreover, both steps require additional tools. A surgeon, thus, needs to have a set of tools at hand in order to take the necessary measures in case of breakage of the insertion tool. If these tools are not available the surgery time is undesirably lengthened.

In consideration of these drawbacks, the object of the present invention is thus to provide an insertion tool which allows for transmitting torque from a drive tool to a dental implant in a safe manner and which at the same time allows easy manipulation of the insertion tool and dental implant in the case of breakage of the insertion tool.

The object is solved by the insertion tool according to claim 1. Preferred embodiments are defined by the dependent claims.

The present invention, thus, relates to an insertion tool for transmitting torque from a drive tool to a dental implant, the insertion tool comprising a tool shaft extending along a longitudinal axis from a coronal end to an apical end, said tool shaft comprising, at the apical end a dental implant engagement section comprising a torque applying means adapted for engaging the dental implant in a torque transmitting manner such that torque can be transmitted from the insertion tool to the implant, and a drive tool engagement section coronal of the dental implant engagement section comprising a primary torque receiving means adapted for engaging the drive tool in a torque transmitting manner such that torque can be transmitted from the drive tool to the insertion tool, and a break zone arranged between the drive tool engagement section and the dental implant engagement section and designed to break upon application of a predetermined amount of torque $T_{break}$.

In dentistry, the term "coronal" refers to the direction towards the crown of a tooth, as opposed to "apical", which refers to the direction towards the tip(s) of the root(s). In the context of an insertion tool, the coronal end thus corresponds to the end which—in use—is remote from the dental implant, whereas the apical end corresponds to the end which is facing the dental implant. The term "proximal" is used herein synonymously with "coronal" and the term "distal" synonymously with "apical".

According to the invention, the tool shaft comprises, between the dental implant engagement section and the break zone, an auxiliary torque receiving means adapted for engaging a drive tool in a torque transmitting manner such that torque can be transmitted from the drive tool to the insertion tool.

Due to the presence of an auxiliary torque receiving means arranged apically of the break zone, the dental implant can be easily manipulated by means of the insertion tool even in the case of breakage of the latter. As the break zone is positioned coronal of the auxiliary torque receiving means, after breaking of the insertion tool this auxiliary means will be located on the part of the insertion tool still in connection with the implant. A drive tool can thus be engaged with this auxiliary torque receiving means in order to further manipulate the implant.

There is, thus, no need to replace the broken insertion tool in order to further manipulate the dental implant. As a consequence, additional tools for releasing the broken insertion tool from the implant as well as an additional intact insertion tool for removing the implant from the bone are not required. This increases the speed and simplicity of removing a dental implant from the bone in the event of an over application of torque.

The auxiliary torque receiving means is located between the dental implant engagement section and the break zone. In embodiments in which the dental implant engagement section is, in use, inserted into an internal bore of an implant therefore, the auxiliary torque receiving means is located outside the dental implant bore.

Typically, the auxiliary torque receiving means is located adjacent to the break zone. After breakage, the auxiliary torque receiving means is, thus, located in the coronal end region of the broken insertion tool and, therefore, is easily accessible by the drive tool.

According to a preferred embodiment, the primary torque receiving means and the auxiliary torque receiving means are adapted to receive torque from the same drive tool. In order to achieve this, it is particularly preferred that the cross-sectional contour of the primary torque receiving means and that of the auxiliary torque receiving means are substantially identical. By "substantially identical" it is meant that both torque receiving means have the same cross-sectional layout of torque receiving surfaces, such that both means can engage with the same torque transmitting surfaces of the driving means of the drive tool. After breakage, the dental implant can thus be manipulated using the same drive tool, and in the same manner, as before breakage. There is thus no need for a surgeon to have an alternative drive tool in case of breakage. Rather, the existing insertion tool and drive tool are sufficient to perform the necessary manipulations.

Unless explicitly stated otherwise, throughout this specification all references to the cross-section of a component refer to the cross-section in a plane perpendicular to the longitudinal axis of that component.

In general, the primary torque receiving means and/or the auxiliary torque receiving means have a non-circular cross-sectional contour having at least one torque receiving surface, as discussed above. For example, they can comprise radially extending grooves and/or protrusions. Preferably however, the contour is that of a regular polygon, more preferably a regular polygon having from 4 to 8 sides, most preferably a hexagon or an octagon. The vertices of the polygon may be rounded or beveled to prevent sharp edges.

Although the non-circular cross-sectional contour can be formed on an interior surface of the torque receiving means, in particular the primary torque receiving means, it is preferred that both the primary and auxiliary torque receiving means have an external non-circular cross-sectional contour. This enables both torque receiving means to be solid, which increases their strength and the overall strength of the insertion tool.

In one preferred embodiment therefore, the primary torque receiving means and/or the auxiliary torque receiving means have the basic form of a non-circular cylinder, the at least one torque receiving surface being formed by the external lateral surface of said cylinder.

In the context of the present invention, the term "cylinder" is to be interpreted broadly as any three-dimensional body enclosed by two basic areas of identical shape lying in parallel planes and being distanced by the cylinder axis running perpendicular to these parallel planes, and bordered laterally by parallel lines connecting the contour of the basic areas. In particular, the term encompasses a prism, more particularly a uniform (i.e. regular) prism, in the following referred to as "regular-polygonal cylinder". The basic areas of the cylinder may alternatively comprise protrusions or indentations such that protrusions or grooves extend the length of the cylinder and form part of its external lateral surface.

It is further preferred that the cylinder comprises at least one flat surface running parallel to the longitudinal axis, said flat surface forming a torque receiving surface. The at least one torque receiving surface can be aligned with a cooperating torque transmitting surface of the driving means of the drive tool in a non-rotational manner, thus allowing an efficient transmission of torque. For example, the torque receiving means can have a standard latch shape for connecting to a dental handpiece.

According to a particularly preferred embodiment, either or both of the torque receiving means has the form of a regular-polygonal cylinder, thus providing a number of planar torque receiving surfaces angularly spaced about the longitudinal axis in a uniform manner. Uniformly spaced surfaces can also be obtained via angularly spaced grooves, protrusions or chamfers. When grooves or protrusions are used these can have planar surfaces or may be curved, for example, to form a Torx® shape. Such uniformly spaced torque receiving surfaces allow torque to be applied to the insertion tool evenly, which further contributes to the efficacy of the torque transmission from the drive tool to the insertion tool.

Due to the rotational symmetry, this embodiment further allows several rotational positions of the drive tool to be engaged with the insertion tool. The insertion tool can thus be accessed by the drive tool from several rotational orientations.

A hexagonal or octagonal cylinder is particularly preferred, allowing for a particularly efficient torque transmission. In the case of a hexagonal cylinder, the torque receiving means comprises six torque receiving surfaces, whereas in the case of an octagon, the torque receiving means comprises eight torque receiving surfaces.

It should be noted that, in use, it is not necessary for all of the torque receiving surfaces to be brought into contact with torque transmitting surfaces of the drive tool. For example, an octagonal cylinder could be fitted within a square sleeve, thus enabling torque to be transmitted to four of the torque receiving surfaces. However, to ensure a good force distribution, it is beneficial for the torque receiving means to be brought into maximum engagement with the drive tool, such that all available torque receiving surfaces are used.

Similarly, the primary and auxiliary torque receiving means may have different numbers or shapes of torque receiving surfaces, while still being capable of engaging the same drive tool. However, as discussed above, it is preferable that the primary and auxiliary torque receiving means have a substantially identical cross-sectional contour.

In respect of embodiments in which the primary and auxiliary torque receiving means each have the basic form of a non-circular cylinder it is therefore preferable that the shape of the basic areas of the cylinders forming the primary and auxiliary torque receiving means are identical. As it is the external lateral surface of the cylinder which forms the one or more torque receiving surface this ensures that the cross-sectional layout of the primary and auxiliary torque receiving surfaces is the same. In such embodiments the primary and/or auxiliary torque receiving means may further include additional, differing features, such as indents, notches, lugs, flanges or other workings on the cylindrical surface which do not form a part of the basic area shape, i.e. these features do not extend the length of the non-circular cylinder. The inclusion of such features in the torque receiving means is not precluded from this preferred embodiment so long as the torque receiving surface(s) are provided by the lateral surface of the base cylinder and not these additional workings. Thus, although the shapes of the basic areas of both torque receiving means are identical, the overall shape of the primary and auxiliary torque receiving means may differ.

In analogy to the torque receiving means, the torque applying means of the insertion tool preferably has a non-circular cross-sectional contour having at least one torque applying surface.

In such embodiments, in order to connect the insertion tool to the dental implant in a non-rotational manner, the latter comprises an anti-rotation means which is complementary to the torque applying means, as discussed above.

In principle, any known combination of torque applying means and anti-rotation means can be used in the present invention.

For example, the implant may comprise an implant bore having radially inwardly protruding projections, each providing an anti-rotation surface which complements the respective torque applying surfaces of the torque applying means. E.g. in the case where the torque applying surfaces are formed by four grooves on the exterior surface of the torque applying means, the implant bore may comprise four projections providing the respective anti-rotation surfaces. Alternatively a section of the implant bore may have a regular polygonal cross-section for cooperation with a polygonal torque applying means.

The torque applying means may be designed for attachment over an external anti-rotation means of the implant. In such cases the torque applying means usually comprises a sleeve or blind bore within which the one or more torque applying surfaces are found.

It is particularly preferred however, in further analogy to the torque receiving means, that the torque applying means is formed by an external non-circular cross-sectional contour. In such embodiments the torque applying means is, in use, inserted into an internal bore of the implant for engagement with the implant anti-rotation means.

In such embodiments it is preferred that the torque applying means has the basic form of a non-circular cylinder, the at least one torque applying surface being formed by the external lateral surface of said cylinder. Preferably the cylinder comprises at least one flat surface running parallel to the longitudinal axis, said flat surface forming a torque applying surface.

In one preferred embodiment, the non-circular cylinder of the torque applying means is formed by a basic area having planar surfaces, protrusions or indentations. This results in the creation of an external cylindrical lateral surface having longitudinally extending chamfers, protrusions or grooves respectively. These chamfers, protrusions or grooves are designed to cooperate with the internal geometry of an implant bore.

In such embodiments, each torque applying surface is thus formed by a chamfer or one or more of the faces of the groove or protrusion. Preferably the chamfers, protrusions or grooves are evenly spaced about the longitudinal axis of the torque applying means in order to provide an even distribution of torque.

In one particularly preferred embodiment the torque applying means comprises a non-circular cylindrical section comprising a plurality of longitudinal grooves, preferably four, on its external lateral surface each having a curved cross-section. Preferably the radius of the curved grooves is between 1 and 1.5 mm. Such a torque applying means is particularly suited for use with an implant comprising an anti-rotation means formed in an internal bore, the anti-rotation means comprising a plurality of radially inwardly projecting protrusions, preferably four.

In another preferred embodiment the torque applying means has a polygonal cross-section, e.g. a hexagon or octagon. Once again the vertices of the polygon can be rounded or beveled to prevent sharp edges. This polygonal cross-section can be in the form of a regular polygonal cylinder, or it may be formed on an internal surface of the torque applying means, for cooperation with an external implant anti-rotation means.

One problem which can occur during use of the insertion tool is jamming between the torque applying and anti-rotation surfaces. Reducing the contact area between the surfaces helps to avoid a friction fit and thus reduces the risk of jamming. On the other hand, a very small contact area between the surfaces concentrates the stresses experienced by the implant anti-rotation means and can lead to deformation. Thus, in all implant system designs a balance must be struck between reducing the contact area while preventing an over concentration of forces.

Therefore, in a preferred embodiment the cross-sectional shape of the torque applying means is non-identical to the cross-sectional shape of the implant anti-rotation means, such that torque transmitting contact only occurs at certain areas. For example, in the above described embodiment in which the torque applying means comprises curved grooves, these may be used in combination with an implant anti-rotation means having protrusions which form planar anti-rotation surfaces.

In an alternative solution to reducing the risk of jamming and distortion, the cross-sectional contour of the torque applying means and the anti-rotation means of the implant can be designed such that the torque applying means can be rotated while in alignment with the implant anti-rotation means, between a first, non-torque transmitting position, in which said torque applying surface and said anti-rotation surface have little or no contact, and a second, torque transmitting position, in which said torque applying surface and said anti-rotation surface are in maximum contact with each other, wherein the angle between the torque applying surface and the anti-rotation surface is less in the second position than in the first position. For example, the torque applying means can comprise at least one pair of torque applying surfaces enclosing an internal angle, preferably of between 150 and 178°, wherein the torque applying surfaces of one pair are arranged, in use, to face one anti-rotation surface of the dental implant.

Thus, each torque applying surface can be rotated—relative to the anti-rotation surface that it is facing—between a first, non-torque transmitting position, and a second, torque transmitting position. According to such embodiments, the rotational play which will inevitably be present is thus used to increase the angular alignment of the surfaces. As the tool can be axially aligned with the implant in the first position this eases connection between the components. It is to be noted that "maximum contact" does not require complete contact between the surfaces, only that the maximum possible contact for the design is achieved.

In this regard, it is referred to European patent publication Nr. 2478864, the content of which is hereby incorporated in its entirety by reference.

The above concept can likewise be applied to the torque receiving means of the insertion tool.

Thus, according to a particularly preferred embodiment, the cross-sectional contour of the primary and/or auxiliary torque receiving means and the driving means of the drive tool are designed such that the torque receiving means can be rotated while in alignment with the driving means, between a first, non-torque transmitting position, in which said torque receiving surface and said torque transmitting surface have little or no contact, and a second, torque transmitting position, in which said torque receiving surface and said torque transmitting surface are in maximum contact with each other, wherein the angle between the torque receiving surface and the torque transmitting surface is less in the second position than in the first position. Thus, also with regard to the interaction between the insertion tool and the drive tool, the risk of deformation can be reduced according to this embodiment.

The break zone of the insertion tool is positioned between the primary and auxiliary torque receiving means and forms a point of weakness on the tool shaft designed to shear or otherwise break upon application of a pre-determined torque $T_{break}$. Preferably the break zone comprises an area of the tool shaft having a reduced diameter. In order to ensure that the tool breaks first in the area of the break zone the break zone usually forms the narrowest diameter of the insertion tool. In other embodiments the break zone could be formed by grooves or score lines running perpendicular to the longitudinal axis. However the break zone is formed, preferably the break zone is designed to break at a torque of above 60 Ncm and/or at a torque less than 130 Ncm, most preferably the pre-determined $T_{break}$ is between 80 and 110 Ncm. When the break zone is formed by an area of narrowed diameter this can also function as a housing connection section, wherein the break zone can be clamped to a housing structure, such that the implant can be indirectly held within a housing. In this way the implant can be prevented from contacting the housing and thus avoid any damage or contamination. In alternative embodiments a housing connection section may be formed by another section of the insertion tool, for example one of the torque receiving means.

According to a preferred embodiment, the dental implant engagement section further comprises, in addition to the torque applying means, a dental implant retention element adapted for releasably holding the dental implant. The dental implant retention element thus provides axial retention and enables the dental implant to be carried on the insertion tool.

In preferred embodiments the retention element is a resilient member that can be connected to the implant via snap or press fit. This improves the ease of connection and disconnection as this can be achieved solely through axial movement of the insertion tool relative to the implant.

The resilient member can be designed to connect to the interior or exterior of the implant, depending on implant design and user wishes. Preferably the resilient member is arranged for insertion into an internal bore of the implant. In this way, contact is avoided with the external surfaces of the implant.

In one embodiment the retention element comprises an annular ring attached to the distal end of the dental implant engagement section. This ring can be open (a split or c-ring) or closed (an o-ring) and is usually made of an elastomeric material, such as PEEK. The ring is sized such that, upon insertion into the implant bore or over the coronal end of the implant, it is compressed, thus forming a press fit, otherwise known as an interference fit. Depending on the internal/external geometry of the implant, i.e. if it contains an undercut or a groove, the ring may also form a snap fit.

In preferred embodiments however the resilient member is an integral part of the dental implant engagement section. This increases the ease of production and prevents disconnection of the member during use.

In one embodiment, the resilient member comprises at least one longitudinal retention arm which is connected at one end to the remainder of the dental implant engagement section such that it is resiliently deflectable towards and/or away from the longitudinal axis.

The term "remainder of the dental implant engagement section" is in this context, thus, to be understood as the portion of said section other than the retention arm(s).

More preferably, the dental implant retention element comprises at least two resilient retention arms which are arranged symmetrically around the longitudinal axis.

The one or more arms can be arranged to engage with the external surface of the implant, for example over a shoulder or within an undercut. In such embodiments the arm(s) must be deflectable away from the longitudinal axis. In other embodiments the one or more arm may be arranged to engage the internal bore of the implant, in which case the arm(s) must deflect towards the longitudinal axis.

In preferred embodiments the one or more arm is arranged to engage the internal bore of an implant. In such embodiments, with regard to the distance from the longitudinal axis, the outermost radial point of each dental implant retention arm defines in its rest position a radius $r_{arm}$, which according to a particularly preferred embodiment is greater than the radius of the implant bore at the axial location at which, in use, the outermost radial point of the dental implant retention arm is located. It is understood that there can be multiple outermost radial points on each arm, however it is preferred that each arm has a single outermost radial point. Thus, in a particularly preferred embodiment the dental implant retention element has two points of engagement with the implant.

When the insertion tool is brought into engagement with the dental implant by inserting the dental implant engagement section into the implant bore, the arms are thereby compressed inwardly and thus deflected towards the longitudinal axis. Since $r_{arm}$ is greater than the radius of the implant bore at the axial location at which the outermost radial point of the arm is located, the arms try to return to their rest position and thereby contact and press outwardly against the internal wall of the implant bore, which creates a press fit, also known as an interference fit, between the dental implant and the insertion tool. Thus, the dental implant is releasably held by the insertion tool and any accidental disconnection of the two components is prevented.

The connection of the insertion tool with the dental implant is particularly stable if the at least one dental implant retention arm is designed such that, in use, its outermost radial point abuts to a threaded section of the implant bore. The groove of the thread provides a roughened surface which enhances retention of the arms.

Alternatively, the outermost radial point of each dental implant retention arm may define in its rest position a radius $r_{arm}$, which is greater than the radius of the implant bore at an axial location coronal of the location at which, in use, the outermost radial point of the dental implant retention arm is located, the radius of the implant bore at this point being greater than the radius at the said coronal location. In other words, when the implant bore comprises an undercut the arms may, upon alignment with this undercut, be able to return to or towards their rest position. This sudden "springing" or "snapping" back of the arms towards their rest position provides the user with feedback that the axial connection between the implant and the insertion tool has been made.

According to a further preferred embodiment, the drive tool engagement section further comprises a drive tool retention element for releasably holding the drive tool. The drive tool retention element thus provides axial retention and enables the insertion tool to be carried on the drive tool. Preferably the drive tool retention element is a resilient member that can be connected to the drive tool via a snap or press fit, and thus connection and disconnection can be achieved solely through axial movement of the insertion tool relative to the drive tool. As with the dental implant retention element, the drive tool retention element can comprise a PEEK ring which provides a snap or press fit when inserted into or over the drive tool. In preferred embodiments however, the drive tool retention element comprises at least one longitudinal retention arm, which is connected at one end to the remainder of the drive tool engagement section such that it is resiliently deflectable towards and/or away from the longitudinal axis. In an analogous manner to the dental implant retention arm, this can either be engaged with the exterior of the drive tool, in which case the arm(s) must flex radially outwards, or to the interior, in which case the arm(s) must flex inwards.

The term "remainder of the drive tool engagement section" is in this context, thus, to be understood as the portion of said section other than the drive tool retention arm.

The use of one or more resilient retention arms to connect the insertion tool to the drive tool is beneficial as it prevents the need for the manufacture of an additional component, namely an annular ring, and enables all parts of the insertion tool to be integrally formed.

This feature is considered inventive in its own right and therefore, viewed from another aspect the present invention provides an insertion tool for transmitting torque from a drive tool to a dental implant, the insertion tool comprising a tool shaft extending along a longitudinal axis from a coronal end to an apical end, said tool shaft comprising, at the apical end a dental implant engagement section comprising a torque applying means adapted for engaging the dental implant in a torque transmitting manner such that torque can be transmitted from the insertion tool to the implant, a drive tool engagement section coronal of the dental implant engagement section and comprising a torque receiving means adapted for engaging the drive tool in a torque transmitting manner such that torque can be transmitted from the drive tool to the insertion tool, wherein the drive tool engagement section further comprises a drive tool retention element for releasably axially holding the drive tool, said retention element comprising at least one longitudinal retention arm which is connected at one end to the remainder of the drive tool engagement section such that it is resiliently deflectable towards and/or away from the longitudinal axis so as to form a press or snap fit with the drive tool.

Preferably the insertion tool further comprises a break zone arranged between the drive tool engagement section and the dental implant engagement section and designed to break at a predetermined amount of torque $T_{break}$. Further, the tool preferably comprises, between the dental implant engagement section and the break zone, an auxiliary torque receiving means adapted for engaging a drive tool in a torque transmitting manner such that torque can be transmitted from the drive tool to the insertion tool. Further preferred features of this aspect of the present invention are as described above and below in relation to the first aspect of the invention.

The one or more drive tool retention arm preferably has a protrusion which engages with a respective undercut in the drive tool, thereby creating a press or snap fit between the drive tool and the insertion tool in order to prevent accidental disconnection of the two components. Preferably the protrusion extends radially outwards and is thus arranged for connection to an internal wall of the drive tool.

In a preferred embodiment the drive tool retention element comprises two longitudinal retention arms diametrically opposed to each other. This provides a secure connection to the drive tool.

The at least one drive tool retention arm can be formed by a longitudinal blind bore extending into the coronal end of the insertion tool, and two longitudinal cuts extending from the external surface of the insertion tool to the blind bore. In this embodiment, the blind bore is typically displaced from the centre, meaning that the axis of the blind bore does not coincide with the longitudinal axis of the insertion tool, and the longitudinal cuts are formed in the region where the distance between the inner surface of the blind bore and the outer surface of the insertion tool is minimal.

Alternatively, the at least one drive tool retention arm can be formed by a single longitudinal cut emanating from the coronal end of the insertion tool and extending along a chord of the cross-section of the coronal end. This embodiment is particularly preferred as it is very simple to manufacture, i.e. by solely providing one single cut per arm.

In preferred embodiments the drive tool engagement section is located at the coronal end of the tool. This keeps the length of the tool to a minimum and reduces the overlap necessary between the insertion tool and drive tool, thus simplifying the connection geometry. Most preferably the above described drive tool retention arm(s) are formed in the primary torque receiving means. This keeps the length of the drive tool engagement section to a minimum.

Preferably, the drive tool retention element comprises two or more drive tool retention arms. It is thereby particularly preferred that each drive tool retention arm is formed by a single longitudinal cut emanating from the coronal end and extending along a chord of the primary torque receiving means. Typically, the arms are regularly spaced about the longitudinal axis. If, for example, the drive tool retention element comprises two arms, they are spaced at an angle of about 180°.

In preferred embodiments the insertion tool is integrally formed. In such embodiments, when the tool comprises a dental implant retention element and/or a drive tool retention element these elements are integral to the drive tool shaft. More generally, the primary torque receiving means, auxiliary torque receiving means and torque applying means preferably form integral parts of the insertion tool shaft. As discussed above, these means are all preferably arranged such that the torque applying and torque receiving surfaces are formed on the exterior surface of the tool.

According to a further aspect the present invention provides a dental implant in combination with the insertion tool of the present invention, the dental implant comprising an anti-rotation means arranged to engage with the torque applying means of the insertion tool in non-rotational manner. The implant may be a one or two part implant. That is, the implant may be designed in use to extend through the gum tissue into the oral cavity to provide direct core support to a dental prosthesis (one part implant) or it may be designed for use with a secondary component, usually called an abutment, in which case it is this secondary component which provides core support to the prosthesis and the implant in use does not extend beyond the gum tissue (two part implant). Preferably the anti-rotation means is located in an internal bore extending axially from the coronal end of the implant.

In preferred embodiments the resilient retention arm(s) of the dental implant engagement section are shaped such that, when the insertion tool is connected to the implant, the outermost radial point of the arm(s) forms an interference fit with the implant bore, preferably a threaded section of the bore. In another embodiment the dental implant engagement section comprises an annular ring which, in use, provides a press or snap fit with the implant bore.

In order to assist with angular alignment of the torque applying means and the anti-rotation means during connection of the insertion tool to the implant, it is preferable that the dental implant and insertion tool are arranged such that the dental implant retention element cannot axially hold the implant until the torque applying means is at least partially axially aligned with the implant anti-rotation means. In other words, the retention element does not engage with the implant to axially hold this until the torque applying means is rotationally aligned with, and thus passes into or over, the implant anti-rotation means. This can be achieved by suitable selection of the length of the retention element, as well as length and position of the anti-rotation and torque applying means.

Preferably the combination further comprises a housing for storing the implant and insertion tool, the housing comprising a clamping section which is sized to firmly retain the break zone of the insertion tool and which provides the sole point of contact between the housing and the insertion tool. Preferably the implant is axially retained on the insertion tool within the housing without contacting the housing.

According to a further aspect the present invention provides a drive tool in combination with the insertion tool of the present invention, the drive tool comprising, at its distal end, a driving means arranged to engage with the primary and, after breakage of the insertion tool at the break zone, auxiliary torque receiving means of the insertion tool in a torque transmitting manner. Preferably the cross-sectional contour of the driving means is substantially identical to the cross-sectional contour of the primary and/or auxiliary torque receiving means.

Preferably the distal end of the drive tool comprises a sleeve, into which the drive tool engagement section can be inserted. The sleeve preferably comprises, on its interior surface, a driving means shaped to engage both of the torque receiving means of the insertion tool in a torque transmitting manner. Further, the sleeve preferably comprises an undercut shaped to cooperate with the drive tool retention element in order to axially retain the insertion tool relative to the drive tool.

The drive tool can be any instrument capable of supplying torque to the insertion tool. For example, it may be a dental handpiece, which is driven by an electric motor, a ratchet, wrench, or a handle to be gripped and turned by a user. It may also comprise an extension piece or adapter; that is, the drive tool may itself be driven by a third component and act only as a connector between the torque source and the insertion tool.

According to a further aspect the present invention comprises a combination of a dental implant, insertion tool and drive tool as described above.

Unless expressly described to the contrary, each of the preferred features described herein can be used in combination with any and all of the other herein described preferred features.

The present invention is further illustrated by way of the figures, of which:

FIG. 6 shows a longitudinal cross section of the insertion tool of FIG. 1 in combination with an implant and drive tool;

FIG. 7 shows a cross-section along the plane D-D shown in FIG. 6;

FIG. 7A shows detail Y of FIG. 7;

FIG. 9 shows a perspective view of a second embodiment of the present invention;

Figure 1:
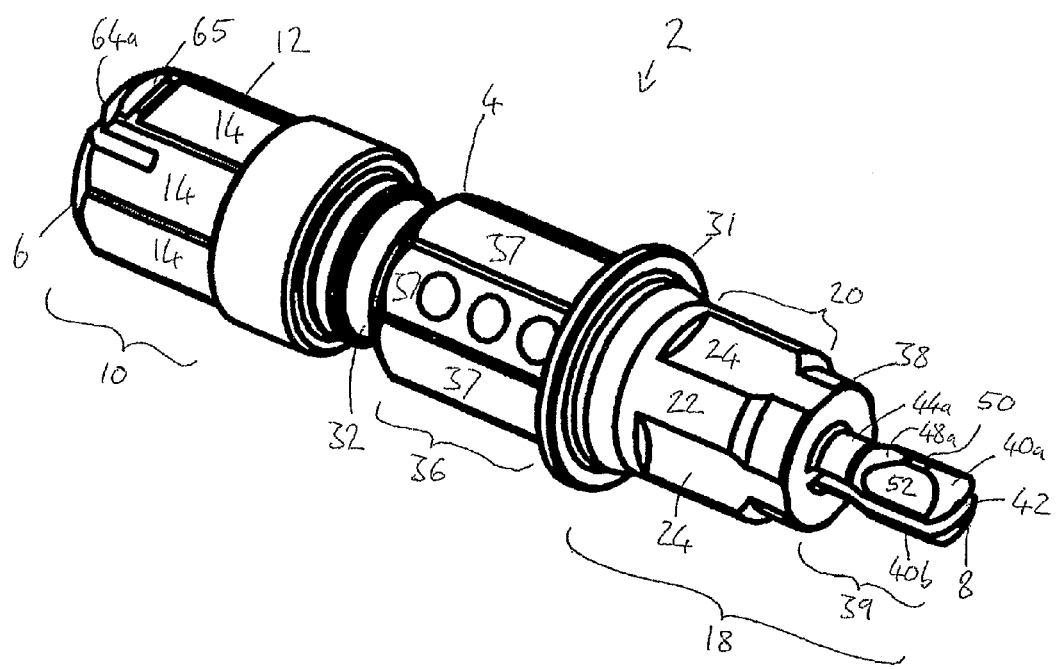
FIG. 1 shows a perspective view of a first embodiment of the present invention.
Figure 2:
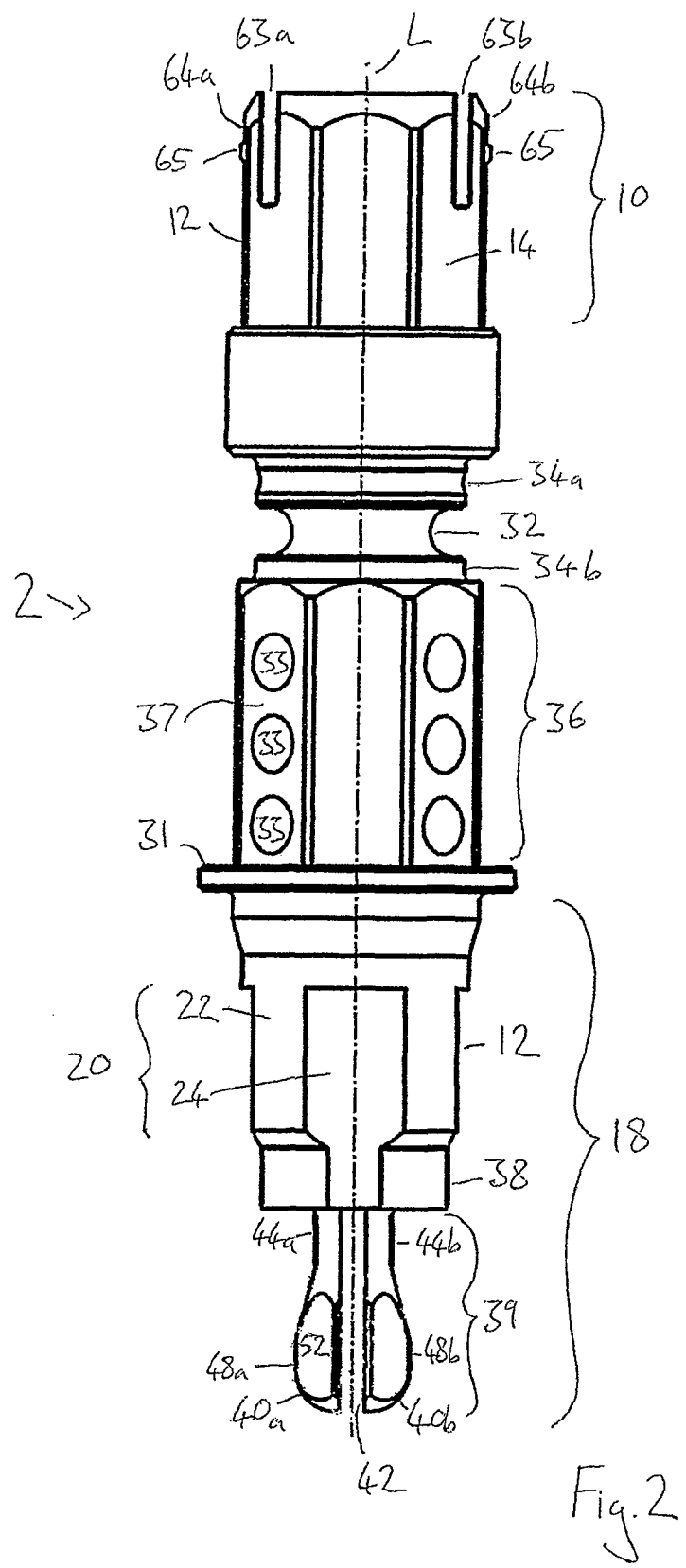
FIG. 2 shows a side view of the embodiment shown in FIG. 1.

As shown in FIGS. 1 and 2, the insertion tool 2 of the present invention comprises a tool shaft 4 extending along a longitudinal axis L from a coronal end 6 to an apical end 8.

In the region of the coronal end 6, a drive tool engagement section 10 is formed, which comprises a primary torque receiving means 12 adapted for receiving torque from a drive tool.

Figure 3:
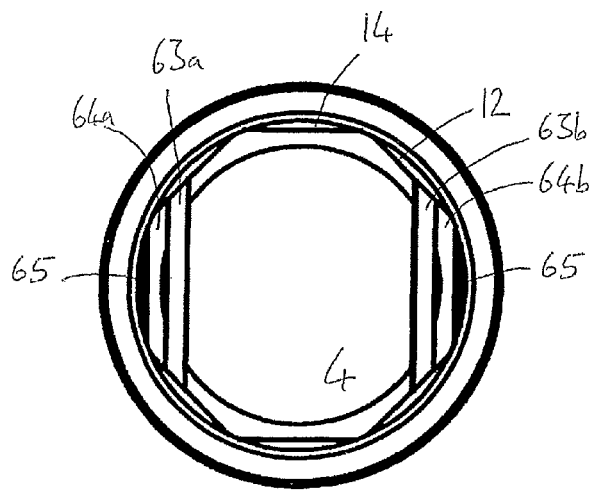
FIG. 3 shows a plan view from the coronal end of the embodiment shown in FIG. 1.

In the embodiment shown, the torque receiving means 12 has the form of a polygonal cylinder, more specifically of an octagonal cylinder, as is particularly shown in FIG. 3. The torque receiving means 12 thus has an external lateral surface having eight flat areas angularly spaced about the longitudinal axis L, each of them forming a torque receiving surface 14. As can be seen, the corners of the octagon are rounded off to prevent sharp edges.

At the apical end 8, a dental implant engagement section is formed which comprises a torque applying means 20 adapted for applying torque—received by the insertion tool at the torque receiving means 12—to the dental implant.

Figure 4:
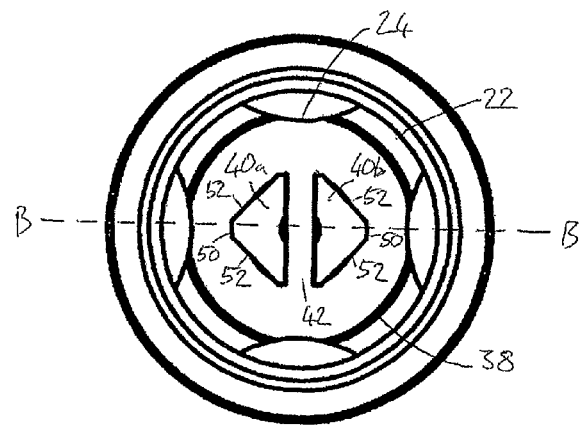
FIG. 4 shows plan view from the apical end of the embodiment shown in FIG. 1.

In the embodiment shown, the torque applying means 20 is a non-circular cylindrical section, the lateral surface 22 of which having four longitudinal grooves 24 angularly spaced around the longitudinal axis L by 90°. Each groove 24 is curved over a radius, such that the cross-section of the grooves in the direction perpendicular to the longitudinal axis L is arc-shaped, as can be seen most clearly in FIG. 4. The curved surface of each groove 24 forms a torque applying surface.

Between the drive tool engagement section 10 and the dental implant engagement section 18, the tool shaft 4 comprises a break zone 32, which is designed to break above a predetermined amount of torque $T_{break}$. In the embodiment shown, the break zone 32 is a narrow section of reduced diameter arranged between two cylindrical sections 34a, 34b of a larger diameter. Break zone 32 forms the narrowest part of the insertion tool 2.

Between the torque applying means 20 and the break zone 32, the tool shaft 4 comprises an auxiliary torque receiving means 36 which is also adapted for receiving torque from a drive tool. In the embodiment shown, the cross-sectional contour of the auxiliary torque receiving means 36 is substantially identical to the primary torque receiving means 12 as both torque receiving means 12, 36 have the basic form of a regular polygonal cylinder and have an identical octagonal basic area shape. The external lateral surface of the auxiliary torque receiving means 36 therefore provides eight flat areas angularly spaced about the longitudinal axis L, each of them forming a torque receiving surface 37.

As discussed previously, the term "substantially identical" requires that both torque receiving means 12, 36 have the same layout of torque receiving surfaces 14, 37 so that they can interact in the same manner with the same drive tool. Therefore, the fact that the torque receiving means differ from one another in certain respects, e.g. arms 64a,b of the primary torque receiving means 12 and orientation holes 33 of the auxiliary torque receiving means 36 (both of which will be discussed in more detail below), does not prevent these from being substantially identical as regards torque receiving surfaces 14, 37.

Thus, the same drive tool can be used for applying torque to either the primary torque receiving means 12 or the auxiliary torque receiving means 36.

The orientation holes 33 which are located on every second auxiliary torque receiving surface 37 indicate to the user the orientation of the anti-rotation surfaces of the attached implant. Thus, the surgeon can insert the implant into the bone at a desired angular orientation.

Apically adjacent to the torque applying means 20, an extension section 38 in the form of a circular cylinder of reduced diameter is formed. From this, a dental implant retention element 39, comprising two identically formed longitudinal dental implant retention arms 40a, 40b, extends to the apical end 8. The dental implant retention arms 40a, 40b are separated from each other by a longitudinal slit 42 having an axis coinciding with the longitudinal axis L of the insertion tool 2; they are thus arranged symmetrically about the longitudinal axis L of the insertion tool 2.

In the longitudinal direction, a first portion 44a, 44b of both dental implant retention arms 40a, 40b, which is directly adjacent to the extension section 38, form stems. Due to the thinness of the first portions 44a, 44b, they are resiliently deflectable towards the longitudinal axis L of the insertion tool.

Figure 5:
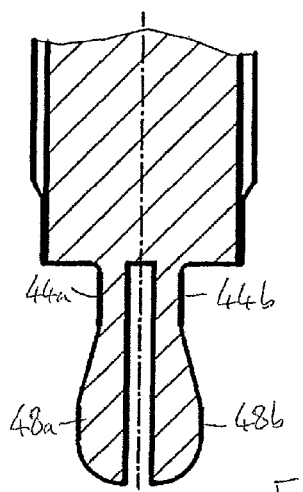
FIG. 5 shows a cross-sectional view of the apical end region of the embodiment shown in FIG. 1 through plane B-B indicated in FIG. 4.

Apical of the first portions 44a, 44b the outer diameter of the dental implant retention arms 40a, 40b, increases and forms a bulge 48a, 48b, as in particular also shown in FIG. 5. The outer surface of the bulge 48a, 48b comprises chamfered surface areas 52 angularly spaced about said axis by 90°. In this embodiment the bulges therefore have a triangular cross-section, although other shapes are also possible, for example, each bulge can have a semi-ellipsoid cross-section. In a rest position, which corresponds to the position shown in FIGS. 1 and 2, the outermost radial points 50 (i.e. the points with the greatest distance from the longitudinal axis L, as in particular shown in FIG. 4) of each dental implant retention arm 40a, 40b define a radius $r_{arm}$. In the embodiment shown, these outermost radial points lie on the surface of the bulge 48a, 48b.

In the specific embodiment shown in FIG. 1-5, the drive tool engagement section 10 further comprises a drive tool retention element comprising two drive tool retention arms 64a, 64b, each of which being formed by a single linear, longitudinal cut 63a, 63b, respectively, emanating from the coronal end 6 and extending along a chord of the octagonal cylinder of the primary torque receiving means 12. This is best seen in FIG. 3. Each arm 64a, 64b comprises on its external surface a protrusion 65. In the embodiment shown, the two drive tool retention arms 64a, 64b are regularly spaced about the longitudinal axis, meaning that they are circumferentially spaced by 180°. Unlike the dental implant retention arms 40a, 40b, the drive tool retention arms 64a, 64b are formed within the primary torque receiving means 12, thus reducing the length of the drive tool engagement section 10.

In use, the insertion tool 2 is brought into engagement with a dental implant 100 by inserting the dental implant engagement section 18 into the implant bore 101, as shown in FIG. 6. The resilient dental implant retention arms 40a, 40b are thereby compressed inwardly and thus deflected towards the longitudinal axis L. Since $r_{arm}$ is greater than the radius of the implant bore 101 at the axial location at which the outermost radial points 50 are located, the dental implant retention arms 40a, 40b try to return to their rest position and thereby contact and press outwardly against the internal wall of the implant bore 101, which creates a press or interference fit between the dental implant 100 and the insertion tool 2. Thus, the dental implant 100 is releasably held by the insertion tool 2 and accidental disconnection of the two components is prevented.

Due to the surface of the bulges 48a, 48b comprising chamfered surface areas 52, the contact area between the dental implant 100 and retention arms 40a, 40b is reduced, thus the press or interference fit between the dental implant and the insertion tool 2 is limited to a degree which allows a relatively easy disconnection of the two components, when desired, by simply pulling the components apart. Further, the variance in pull off force caused by manufacturing tolerances is reduced. Likewise, the chamfered surface areas 52 allow the dental implant engagement section 18 of the insertion tool 2 to be introduced into the implant bore without exerting too much force.

In the present embodiment the insertion tool 2 is prevented from being inserted too deeply into the implant bore 101 by shoulder 31, which in use abuts against the coronal end 104 of the implant 100. However, in other embodiments the resilient member may form a snap fit to the implant, which provides the user with feedback that the correct alignment has been achieved, or an abutment surface may be formed within the implant bore 101. In further embodiments the torque applying means may be placed over an external implant anti-rotation means such that it abuts against an external surface of the implant.

When the insertion tool 2 is inserted into the implant bore 101, the two components are fixed anti-rotationally, which ultimately allows torque to be transmitted to the dental implant. To this end, the implant bore 101 comprises an anti-rotation means 102 having four radially inwardly protruding projections 103, each providing anti-rotation surfaces complementary to the respective torque applying surfaces of the torque applying means 20.

This can be seen most clearly in FIG. 7, which shows a cross-section through the aligned anti-rotation means 102 and torque applying means 20. Each of the projections 103 is housed within a groove 24 of the torque applying means 20. When the insertion tool 2 is rotated in the direction indicated in FIG. 7 the surface of the grooves 24 is brought into contact with the protrusions 103 as shown in detail in FIG. 7A. This contact occurs in the same area of each groove and protrusion, thus providing an evenly distributed transmission of torque. As can be seen in FIG. 7A, minimal surface contact is achieved between the groove 24 and protrusion 103, thus reducing the possibility for jamming.

As can be seen in FIG. 6, the length of the dental implant retention arms 40a,b is short enough that these will not engage the narrow section of implant bore 101 with which they form a press fit until the grooves 24 and projections 103 are aligned, thus allowing the torque applying means to fit into the implant anti-rotation means 102. This eases the correct connection of the components.

For applying torque to the insertion tool 2, the primary torque receiving means 12 is brought into engagement with a drive tool 200.

The drive tool 200 has at its distal end a hollow sleeve 201 into which the drive tool engagement section 10 of the insertion tool 2 can be inserted. Flat surface areas on the interior surface of sleeve 201 form torque transmitting surfaces 202. In the present embodiment these surfaces form an octagonal cross-section matching the torque receiving surfaces 14 of the insertion tool 2. When engaged, the torque transmitting surfaces 202 of the drive tool 200 and the torque receiving surfaces 14 of the insertion tool 2 are in alignment with each other, thus providing for torque transmission between the components.

Protrusions 65 extend outwards from the torque receiving surfaces 14 and therefore, as the drive tool engagement section 10 is inserted into the sleeve 201 and past the torque transmitting surfaces 202, flexible arms 64a, 64b are bent towards the longitudinal axis L. Sleeve 201 further comprises, coronal of the torque transmitting surfaces 202, an undercut 205. This area of increased diameter enables the arms 64a, 64b of the drive tool engagement section 10 to spring or snap back to their rest position once protrusions 65 are brought into alignment with the undercut 205. This provides the user with feedback that the insertion tool 2 has been correctly aligned with the drive tool 200 and furthermore creates an axial retention between these two components.

For inserting the dental implant into the implantation site, torque is applied from the drive tool 200 to the insertion tool 2 which transmits torque to the dental implant 100. Torque can be applied to the drive tool 200 via the human hand gripping handle 203. Handle 203 comprises angularly spaced longitudinal grooves 204, which can alternatively be engaged by a suitably shaped wrench or ratchet.

Figure 8A:
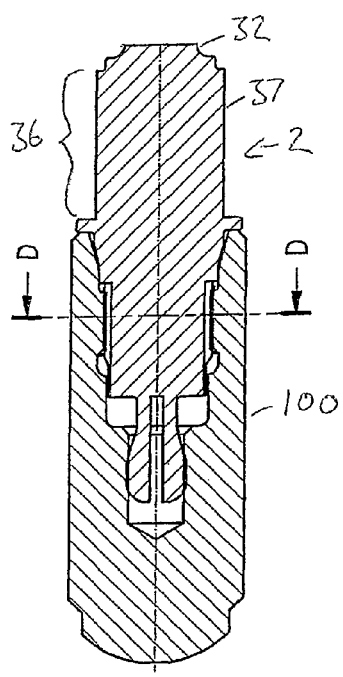
FIG. 8A shows the cross-section of FIG. 6 after breaking of the insertion tool at the break point.

If a predetermined amount of torque is exceeded, the insertion tool 2 breaks at the break zone 32, which safeguards that neither the dental implant nor the bone is damaged. This situation is shown in FIG. 8A.

Figure 8B:
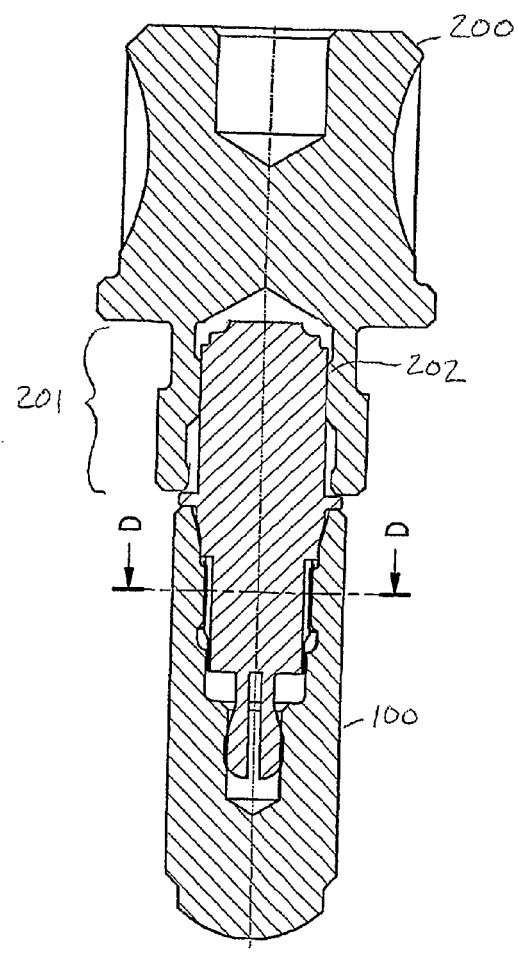
FIG. 8B shows the cross-section of FIG. 8A after connection of the drive tool to the auxiliary torque receiving means.
Figure 10:
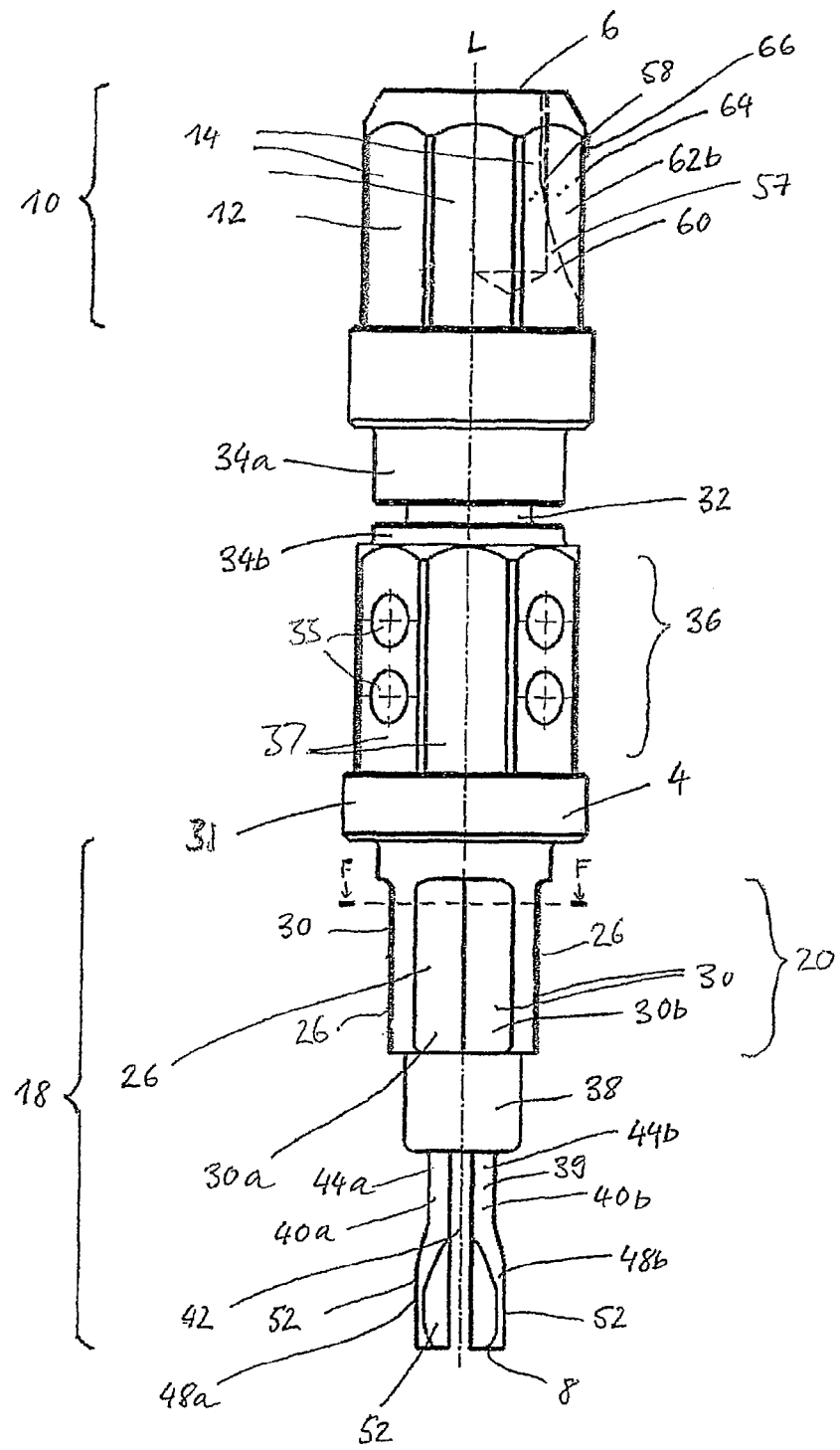
FIG. 10 shows a side view of the embodiment shown in FIG. 9.

Due to the provision of a break zone 32, the insertion tool 2 breaks at a well-defined point. The cylindrical section 34a coronal of the break zone 32 has a narrower diameter that the drive tool engagement section 10 and thus provides a gripping point for the user when removing the coronal part of the broken insertion tool 2 from the drive tool 200. After breaking, the auxiliary torque receiving means 36 is located in the coronal end region of the apical part of the broken insertion tool 2. It can thus be easily accessed by the drive tool 200 for further manipulation of the dental implant 100. As shown in FIG. 8B, the hollow sleeve 201 of drive tool 200 can now be inserted over the auxiliary torque receiving means 36. As the auxiliary torque receiving means is substantially identical in cross section to the primary torque receiving means 12, the torque receiving surfaces 37 are brought into contact with the torque transmitting surfaces 202 of the driving means in an identical manner as the primary torque receiving surfaces 14.

Depending on the direction of the torque applied, the dental implant can then be inserted further into or removed from the implantation site by means of the same drive tool initially used.

FIGS. 9-12 show an embodiment of the present invention which differs from the embodiment shown in FIG. 1 mainly in the design of the drive tool engagement section 10 and in the torque applying means 20.

The primary torque receiving means 12 according to FIG. 9 again has the form of an octagonal cylinder. However, the arms 64a, 64b of the first embodiment are replaced by a single resilient flexible arm created in the torque receiving means 12. As in particular shown in FIGS. 10 and 12, the drive tool engagement section 10 comprises a blind bore 58 extending from the coronal end 6 in a direction parallel to the longitudinal axis L, but displaced from the centre of the insertion tool 2. In the region where the distance between the inner surface of the blind bore 58 and the outer surface of the drive tool engagement section 10 is at its narrowest, two linear longitudinal cuts 62a, 62b extending from the external surface of the insertion tool to the blind bore are formed. Thus, a longitudinal drive tool retention arm 64 is formed which is deflectable towards the longitudinal axis L and thus functions as a snapper arm. On its outer surface, the snapper arm comprises a projection 66 designed to snap into an undercut in the drive tool, although alternatively a press fit could be created, depending on the length of the projection 66 and depth of the undercut.

As mentioned, the embodiment shown in FIGS. 9-12 further differs from the one shown in FIG. 1 in the design of the torque applying means 20.

Figure 11:
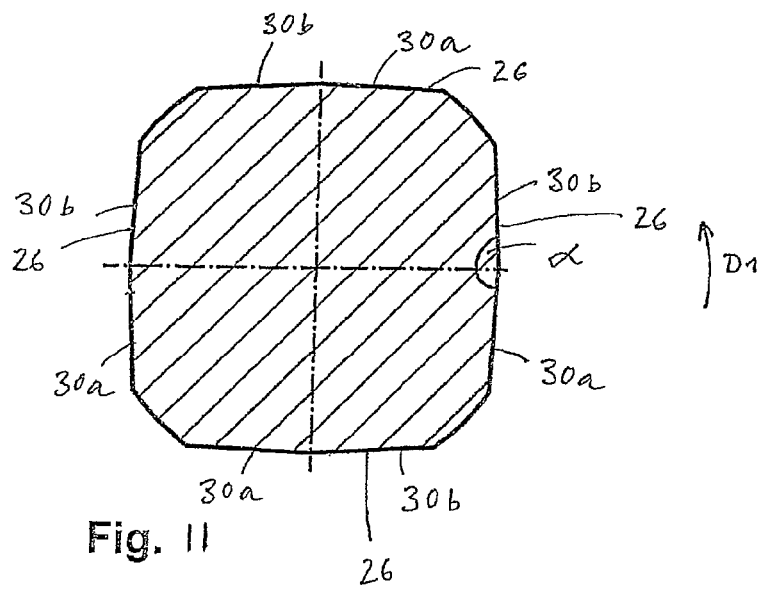
FIG. 11 shows a cross-section through plane F-F indicated in FIG. 10.
Figure 12:
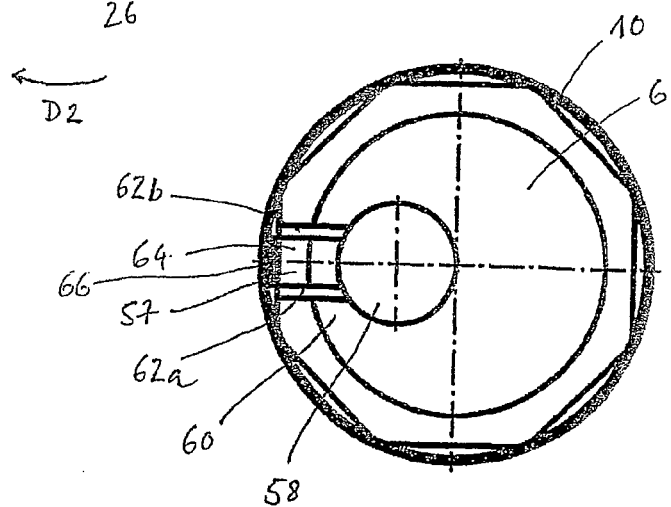
FIG. 12 shows a plan view from the coronal end of the embodiment shown in FIG. 9.

In particular, the grooves 24 of the torque applying section 20 are replaced by chamfers 26, which in each case are subdivided into two paired torque applying surfaces 30a, 30b enclosing an internal angle α (alpha) of about 174°, as in particular shown in FIG. 11.

When inserted into dental implant bore 101 of FIG. 6 for example, the two torque applying surfaces 30a, 30b of one chamfer 26, face the same anti-rotation projection 103 of the dental implant. When the insertion tool 2 is rotated in one direction D1, one torque applying surface 30a from each pair is brought into its maximum possible contact with the respective anti-rotation projection 103 of the dental implant for the transmission of torque, whereas—when it is rotated in the other direction D2—the other torque applying surface 30b is brought into maximum contact with the respective anti-rotation projection 103 of the dental implant in order to enable torque to be applied in the opposite direction. In this embodiment, there is thus surface-to-surface contact. This allows a very efficient transmission of torque with a reduced risk of deformation of the implant anti-rotation means while the maximum contact area is controlled in order to prevent jamming of the insertion tool within the implant bore.

One additional, minor change in this embodiment is the chamfered surface areas 52 of the dental implant retention arms 40a, 40b. These chamfers 52 are created such that they are in longitudinal alignment with chamfers 26 of the torque applying means 20. This is in contrast to the chamfers 52 of the embodiment of FIG. 1, in which the chamfers 52 are in longitudinal alignment with the circular areas of lateral cylindrical surface 22. This alteration in alignment has no practical effect on their function however.

Figure 13:
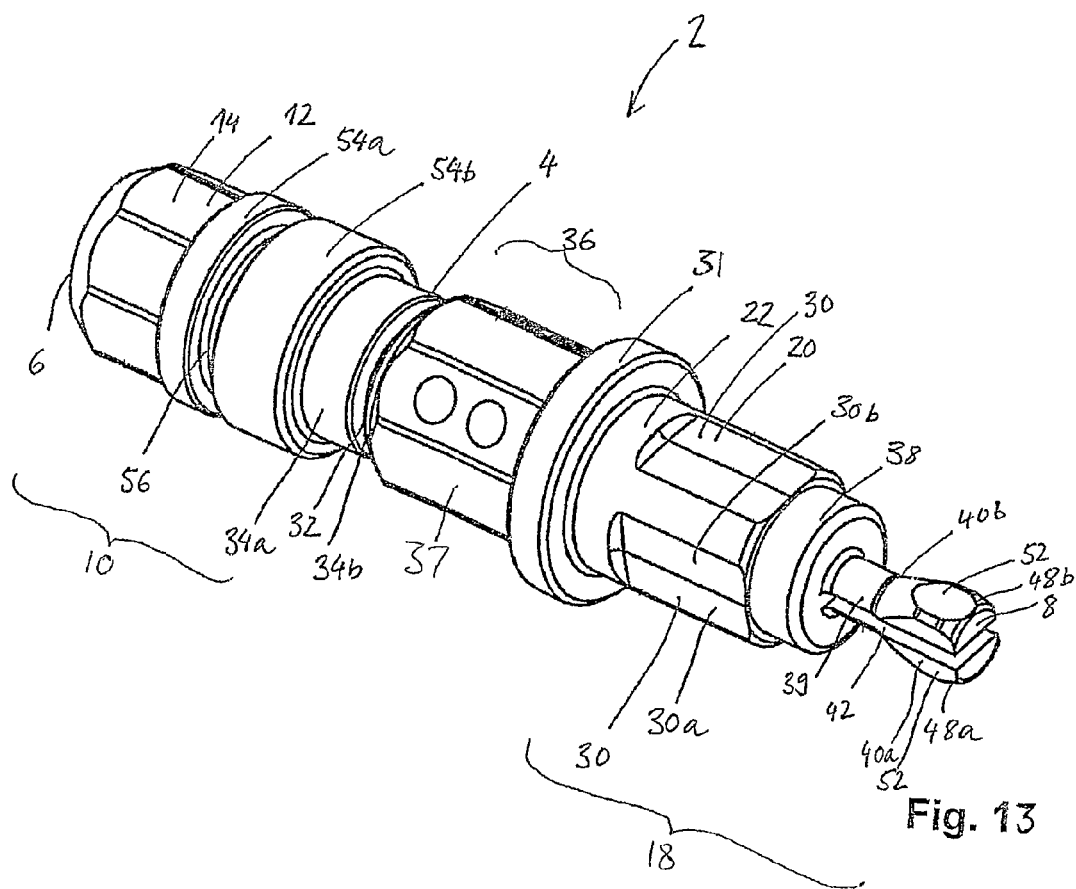
FIG. 13 shows a perspective view of a further embodiment of the present invention.

FIG. 13 relates to a further embodiment in which the drive tool retention element of the drive tool engagement section 10 comprises a PEEK (polyether ether ketone) ring (not shown). In order to hold the PEEK ring in place, the tool shaft comprises two clamping sections 54a, 54b, a first clamping section 54a being arranged apically adjacent to the primary torque receiving means 12 and a second clamping section 54b being located apically from the first clamping section 54a and being separated from the first clamping section by a concavely formed ring contact section 56, having a smaller diameter than clamping sections 54a, 54b. The PEEK ring is positioned in the ring contact section 56 and is thus sandwiched between and held in place by the clamping section 54a, 54b.

The outer diameter of the PEEK ring protrudes from the outer diameter of the clamping sections 54a, 54b. The surface of the protruding portion of the ring allows a friction-fit or snap fit with the internal surface of the sleeve of a drive tool to be established.

Alternatively to a PEEK ring, a ring of any other polymeric material suitable for the purpose described above can be used.

The above described embodiments are for illustrative purposes only and the skilled man will realize that many alternative arrangements are possible which fall within the scope of the claims. In particular, the torque applying means may be designed to engage an external boss of the implant. In such cases the torque applying means will form a sleeve having torque applying surfaces on its inner surface, in a similar manner to the sleeve 201 of drive tool 200. Alternatively or additionally the dental implant retention element may be an o- or c-ring designed for press or snap fit to the implant bore, or may comprise one or more resilient arms designed to connect to the exterior of the implant. Any known form and shape of torque applying means and torque receiving means can be used in the present invention.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. An insertion tool for transmitting torque from a drive tool to a dental implant, the insertion tool comprising a tool shaft extending along a longitudinal axis from a coronal end to an apical end, said tool shaft comprising
   at the apical end a dental implant engagement section comprising a torque applying means adapted for engaging the dental implant in a torque transmitting manner such that torque can be transmitted from the insertion tool to the implant, and
   a drive tool engagement section coronal of the dental implant engagement section and comprising a primary torque receiving means adapted for engaging the drive tool in a torque transmitting manner such that torque can be transmitted from the drive tool to the insertion tool, and
   a break zone arranged between the drive tool engagement section and the dental implant engagement section and designed to break upon application of a predetermined amount of torque $T_{break}$,
   wherein the tool shaft comprises, between the dental implant engagement section and the break zone, an auxiliary torque receiving means adapted for engaging a drive tool in a torque transmitting manner such that torque can be transmitted from the drive tool to the insertion tool, and
   wherein a cross-sectional contour of the primary torque receiving means and of the auxiliary torque receiving means are substantially identical.

2. Insertion tool according to claim 1 wherein, the primary torque receiving means and auxiliary torque receiving means each has a non-circular cross-sectional contour having at least one torque receiving surface.

3. Insertion tool according to claim 2, wherein, the primary torque receiving means and/or the auxiliary torque receiving means have the basic form of a non-circular cylinder, the at least one torque receiving surface being formed by the external lateral surface of said cylinder.

4. Insertion tool according to claim 1, wherein the torque applying means has a non-circular cross-sectional contour having at least one torque applying surface.

5. Insertion tool according to claim 4, wherein the torque applying means has the basic form of a non-circular cylinder, the at least one torque applying surface being formed by the external lateral surface of said cylinder.

6. Insertion tool according to claim 1, wherein the break zone comprises an area of the tool shaft having the narrowest diameter of the insertion tool.

7. Insertion tool according to claim 1, wherein the dental implant engagement section further comprises a dental implant retention element adapted for releasably holding the dental implant, the dental implant retention element comprising at least one longitudinal retention arm which is connected at one end to the remainder of the dental implant engagement section such that it is resiliently deflectable towards the longitudinal axis.

8. Insertion tool according to claim 1, wherein the drive tool engagement section further comprises a drive tool retention element for releasably holding the drive tool, said drive tool retention element comprising at least one longitudinal retention arm, which is connected at one end to the remainder of the drive tool engagement section such that it is resiliently deflectable towards the longitudinal axis.

9. Insertion tool according to claim 8, wherein the at least one retention arm is formed by a longitudinal blind bore extending into the coronal end, and two longitudinal cuts extending from the external surface of the insertion tool to the blind bore.

10. Insertion tool according to claim 8, wherein the at least one retention arm is formed by a single longitudinal cut emanating from the coronal end and extending along a chord of the cross-section of the coronal end.

11. Insertion tool according to claim 8, wherein the at least one retention arm is formed in the primary torque receiving means.

12. An insertion tool for transmitting torque from a drive tool to a dental implant according to claim 1, wherein the drive tool engagement section further comprises a drive tool retention element for releasably axially holding the drive tool, said retention element comprising at least one longitudinal retention arm which is connected at one end to the remainder of the drive tool engagement section such that it is resiliently deflectable towards and/or away from the longitudinal axis so as to form a press or snap fit with the drive tool.

13. A dental implant in combination with an insertion tool as claimed claim 1, the dental implant comprising an anti-rotation means arranged to engage with the torque applying means of the insertion tool in a non-rotational manner.

14. A drive tool in combination with the insertion tool as claimed in claim 1, the drive tool comprising, at its distal end, a driving means arranged to engage with the primary and, after breakage of the insertion tool at the break zone, auxiliary torque receiving means of the insertion tool in a torque transmitting manner.

* * * * *